US00PP14246P29

(12) United States Plant Patent
Lucas

(10) Patent No.: US PP14,246 P2
(45) Date of Patent: Oct. 21, 2003

(54) EUPHORBIA PLANT NAMED 'VANILLA SWIRL'

(50) Latin Name: *Euphorbia characias*
Varietal Denomination: Vanilla Swirl

(76) Inventor: Neil Lucas, Knoll Gardens, Hampreston, Limborne, Dorset BH21 7ND (GB)

( * ) Notice: Subject to any disclaimer, the term of this patent is extended or adjusted under 35 U.S.C. 154(b) by 0 days.

(21) Appl. No.: 10/241,541

(22) Filed: Sep. 11, 2002

(51) Int. Cl.[7] ..... A01H 5/00
(52) U.S. Cl. ..... Plt./302
(58) Field of Search ..... Plt./302

*Primary Examiner*—Bruce R. Campell
*Assistant Examiner*—Susan B. McCormick

(57) ABSTRACT

A new cultivar of Euphorbia named 'Vanilla Swirl' that is distinguished by a compact rounded habit, variegated foliage exhibiting white margins and green centers, and bright red stems that fade to pink. In combination these traits set 'Vanilla Swirl' apart from all other existing varieties of Euphorbia known to the inventor.

4 Drawing Sheets

Genus: Euphorbia.
Species: *characias.*
Denomination: 'Vanilla Swirl'.

BACKGROUND OF THE INVENTION

The present invention relates to a new and distinct cultivar of spurge, a hardy perennial that is grown for its unique foliage and its use as an ornamental landscape plant. The new invention is known botanically as *Euphorbia characias* and will be referred to hereinafter by the cultivar name 'Vanilla Swirl'.

'Vanilla Swirl' was discovered by the inventor in 1998 in Bury St. Dorset, United Kingdom as a self-set seedling found in a cultivated area of the inventor's garden beneath a small group of *Euphorbia characias.* The female or seed parent is presumed to be *Euphorbia characias* and the male or pollen parent is presumed to be *Euphorbia characias.* 'Vanilla Swirl' was selected by the inventor for its variegated leaves that exhibit green centers and irregular cream-white margins, compact rounded growth habit, bright red stems in spring that fade to pink by summer and consistent variegation of the foliage without reversion to green. Rarely occurring flowers are held on terminal stems and born axial to the leaf joints with two cyathia cupped by two basally fused floral leaves, also called involucres. The margins of the leaves are whitest in spring and become cream-white in summer.

The closest comparison plant is Euphorbia 'Burrows Silver' (not patented). 'Vanilla Swirl' is distinguishable from 'Burrows Silver' by its compact habit, finer foliage, rare flowering, and no reversion to green.

The first asexual reproduction of 'Vanilla Swirl' was accomplished by the inventor in Dorset, United Kingdom in 1998. The method used was softwood cuttings. Since that time subsequent generations have been determined stable and true to type.

SUMMARY OF THE INVENTION

The following traits have been repeatedly observed and represent the distinguishing characteristics of the new Euphorbia cultivar. These traits in combination distinguish 'Vanilla Swirl' from all other existing varieties of Euphorbia known to the inventor. 'Vanilla Swirl' has not been tested under all possible conditions and phenotypic differences may be observed with variations in environmental, climatic, and cultural conditions, however, without any variance in genotype.

1. Euphorbia 'Vanilla Swirl' exhibits a compact rounded growth habit.
2. Euphorbia 'Vanilla Swirl' exhibits rare flowering.
3. Euphorbia 'Vanilla Swirl' exhibits variegated, fine leaves with green centers and irregular cream-white margins that are whitest in spring turning cream-white in summer.
4. Euphorbia 'Vanilla Swirl' exhibits bright red stems in spring fading to pink by summer.
5. Euphorbia 'Vanilla Swirl' exhibits consistently variegated foliage without reversion to green.

BRIEF DESCRIPTION OF THE DRAWINGS

The accompanying drawings illustrate the distinguishing traits of the new Euphorbia cultivar 'Vanilla Swirl'. The photographs were taken in spring and summer of plants in two-litre containers that were 36-month-old and grown out-of-doors in a cultivated area of Dorset, United Kingdom. No chemicals were administered to the plants.

The drawing on sheet 1 illustrates the entire plant in spring from a side perspective.

The drawing on sheet 2 illustrates a close-up view of the white foliage margins in spring.

The drawing on sheet 3 illustrates the change to cream-white margins in summer.

The drawing on sheet 4 is a close-up view of the flower in spring. Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new Euphorbia cultivar 'Vanilla Swirl'. Observations, measurements, values and comparisons were collected in Dorset, United Kingdom from plants that were 36 months old and grown out-of-doors in two-litre containers. Color determinations are made in accordance with The 1995 Royal Horticultural Society Colour Chart from London England, except where general color terms of ordinary dictionary significance are used. The growing requirements of the new variety are similar to the species and there are no known growing problems, diseases or pests.

Botanical classification: *Euphorbia characias* 'Vanilla Swirl'.
Species: *characias.*
Common name: Spurge.
Parentage: Euphorbia 'Vanilla Swirl' is the naturally occurring self-set seedling that resulted from spontaneous self-hybridization. The parents are presumed to be the following plants:
*Female parent.*—*Euphorbia characias.*
*Male parent.*—*Euphorbia characias.*
Propagation method: Softwood cuttings.
Rooting habit: Fibrous and fleshy.
Time to develop roots: In California 2–3 weeks are required for roots to develop on an initial cutting at 15° Centigrade air temperature.
Crop time: In California 12–16 months are required to develop a finished two-litre container from a rooted cutting.
Growth habit: Compact slow-growing growth habit.
Use: Ornamental landscape plant.
Type: Perennial herb.
Vigor: Low, slow-growing.
Height of plant: 70–90 cm. in height.
Width of plant: 60–90 cm. in width.
Cultural requirements: Plant in three quarters to full sunlight and free-draining soil.
Diseases and pests: None known to the inventor.
Hardiness: Hardy to minus 8° Centigrade.
Stem:
*Branching habit.*—Basal branching and upright.
*Stem colors.*—The stems are blotched with varied colors that range from the basic color 68D to a paler pink that is 73D and 66C. The pink base transitions to brown 172C with green patches that are 145C. Where the stem is obscured by leaves the colors of the stem are 145D and 150D.
*Stem shape.*—Cylindrical to columnar.
*Stem width.*—8–11 mm. in width.
*Stem length.*—28–30 cm. in length.
*Stem surface.*—The surface area between bundle scars and the surfaces where bundle scars are absent is glabrous. Basal surface to mid-stem is heavily covered with bundle scars.
*Bundle scars.*—Present on stem surface.
*Shape of bundle scars.*—Linear shaped.
*Dimensions of bundle scars.*—2–5 mm. in width and 2 mm. in height.
*Color of bundle scars.*—201D.
*Quantity of bundle scars.*—Numerous amounting to approximately 42 on a 20 cm. long stem.
*Other.*—Stems exude a white milky sap that can be toxic and may elicit dermal irritation.
Foliage:
*Type.*—Evergreen.
*Leaf arrangement.*—Most leaves have spiral arrangement. On the smaller stems some leaves are alternate.
*Internode dimensions.*—Where leaves are alternate internode is 12 mm. and where leaves spiral internode is 1–2 mm.
*Leaf division.*—Simple.
*Leaf shape.*—Gladiate.
*Mature leaf length.*—110 mm. in length.
*Mature leaf width.*—13 mm. in width.
*Young leaf length.*—80–90 mm. in length.
*Young leaf width.*—5–8 mm. in width.
*Leaf apex.*—Apiculate.
*Quantity of leaves.*—An average of 250 leaves per branch.
*Leaf venation pattern.*—Parallel with a prominent central vein.
*Margin.*—Entire.
*Leaf surface* (*abaxial surface*).—Most of the surface area is glabrous but there is a light amount of pubescence near the central vein.
*Leaf surface* (*adaxial surface*).—Most of the surface area is glabrous but there is a light amount of pubescence near the central vein.
*Leaf attachment.*—Sessile.
*Leaf color in spring* (*adaxial surface*).—The center ranges in green from 133A and 133B to 133C while the margin is 155B.
*Leaf color in spring* (*abaxial surface*).—The center ranges in green from 133A and 133B to 133C while the margin is 155B.
*Leaf color in summer* (*adaxial surface*).—The center is 131A and the margin is 158A,B.
*Leaf color in summer* (*abaxial surface*).—The center is 131A and the margin is 158A,B.
*Other.*—There is a milky white fluid that exudes from the leaves if they are torn or bruised. This substance may illicit dermal irritation.
Flower:
*Type.*—Inflorescence.
*Dimensions of inflorescence.*—8–15 mm. in diameter and 5–8 mm. in height.
*Inflorescence.*—Cyathium.
*Flowering season.*—Spring.
*Flower aspect.*—Facing upward and outward.
*Peduncle dimensions.*—36 mm in length and 2 mm. in width.
*Peduncle color.*—133A,B.
*Peduncle surface.*—Glabrous.
*Petals.*—Apetalous.
*Sepals.*—Apetalous.
*Floral leaf attachment.*—Connate perfoliate.
*Dimensions of floral leaves.*—12 mm. in length and 2 cm. in width.
*Shape of floral leaf.*—Reniform.
*Color of floral leaf.*—Center is 133A,B,C and margins are 158C,D.
*Number of floral leaves.*—Two in number.
*Fused or unfused.*—Basally fused.
*Number of cyathium.*—Two cupped within the center of two basally fused floral leaves.
*Margins.*—Entire.
*Shape of cyathium.*—Cupulate.
*Number of floral leaves on each cyathium.*—Two.
*Fused or unfused.*—Basally fused.
*Color of cyathium.*—Mostly 155D with a splash of green 133A and 133C in the center.
*Dimensions of cyathium.*—5–8 mm. in length and 8–15 mm. in diameter.

*Flower fragrance.*—Absent.
*Bud shape.*—Globose.
*Bud dimensions.*—4–6 mm. in diameter and 3–5 mm. in length.
*Bud color.*—155D.

Reproductive organs:
*Stamen color.*—155C.
*Stamen dimensions.*—Less than 0.50 mm. in length and 1 mm. in diameter.
*Anther shape.*—Ovoid.
*Anther color.*—155C.
*Anther dimensions.*—1 mm. in width and 2 mm. in length.
*Pollen.*—Minimal amount.
*Ovary.*—None observed.
*Color of pistil.*—155C.
*Style color.*—155C.
*Stigma color.*—155C.
*Dimensions of stigma.*—Less than 0.75 mm. in width and less than 0.75 mm. in height.

Seed: No seed has been observed. The plant is presumed to be sterile.

I claim:

1. A new and distinct cultivar of Euphorbia plant named 'Vanilla Swirl' as described and illustrated.

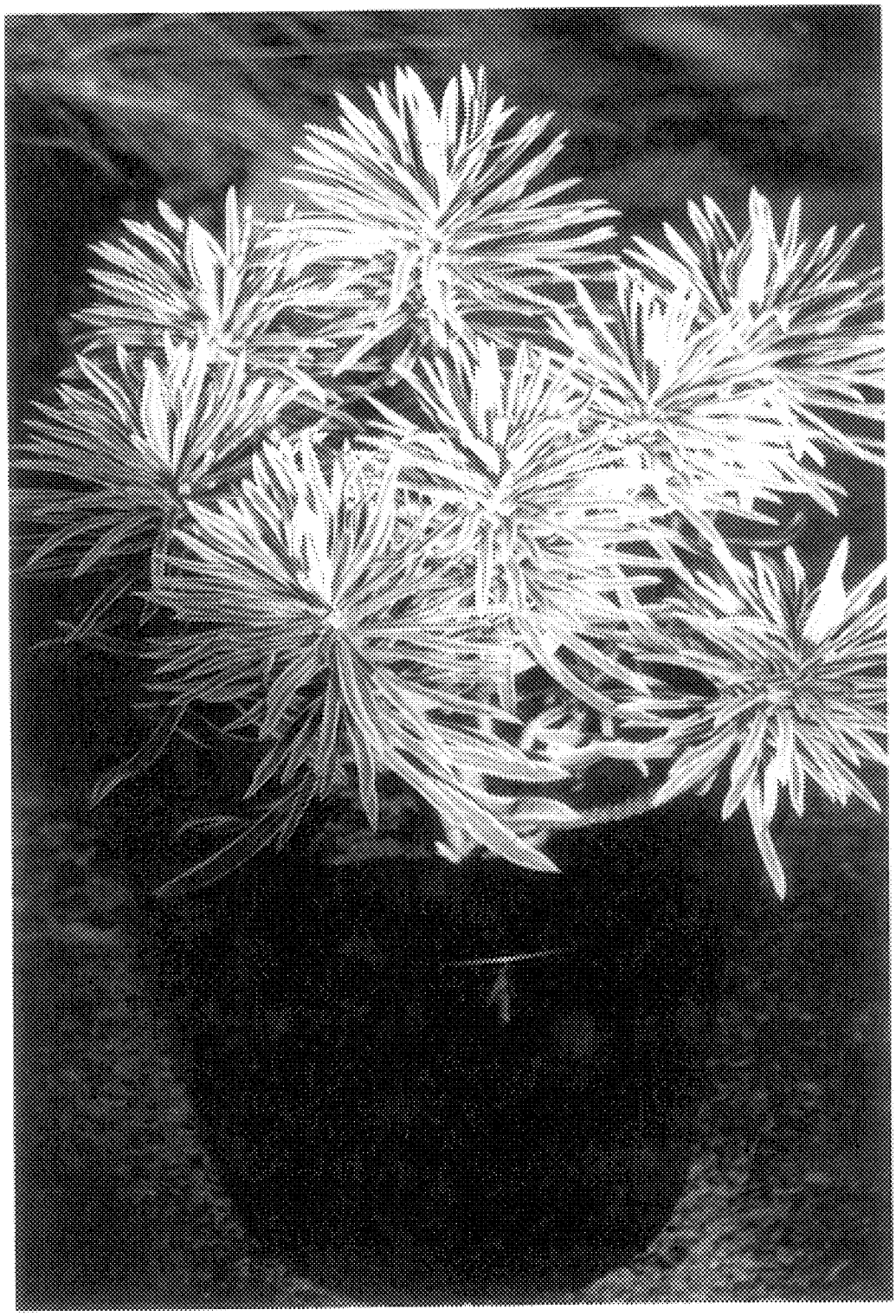

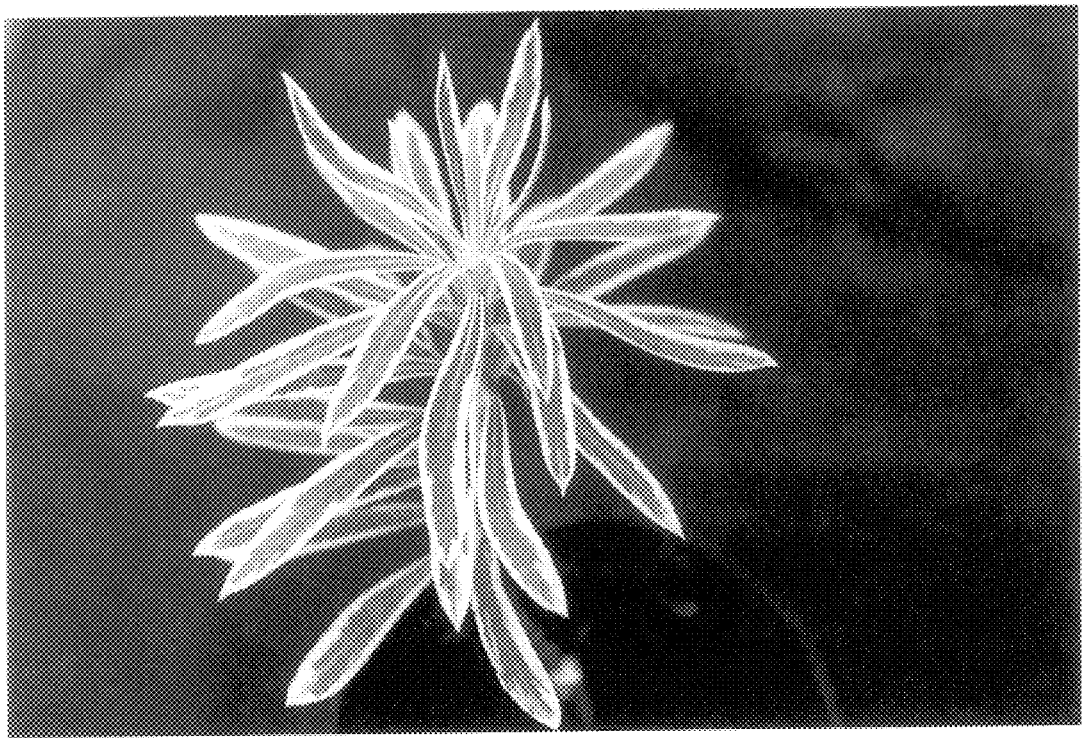

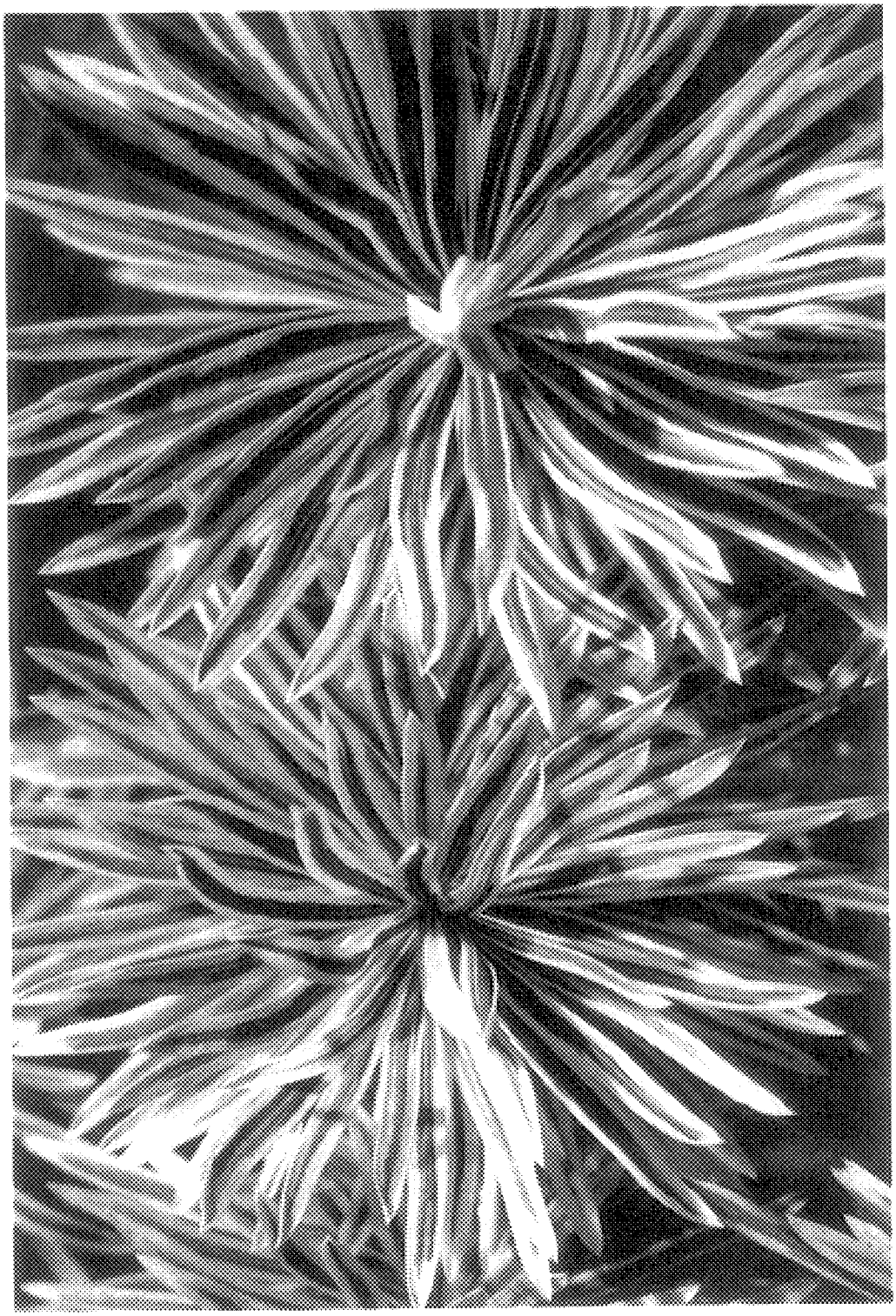

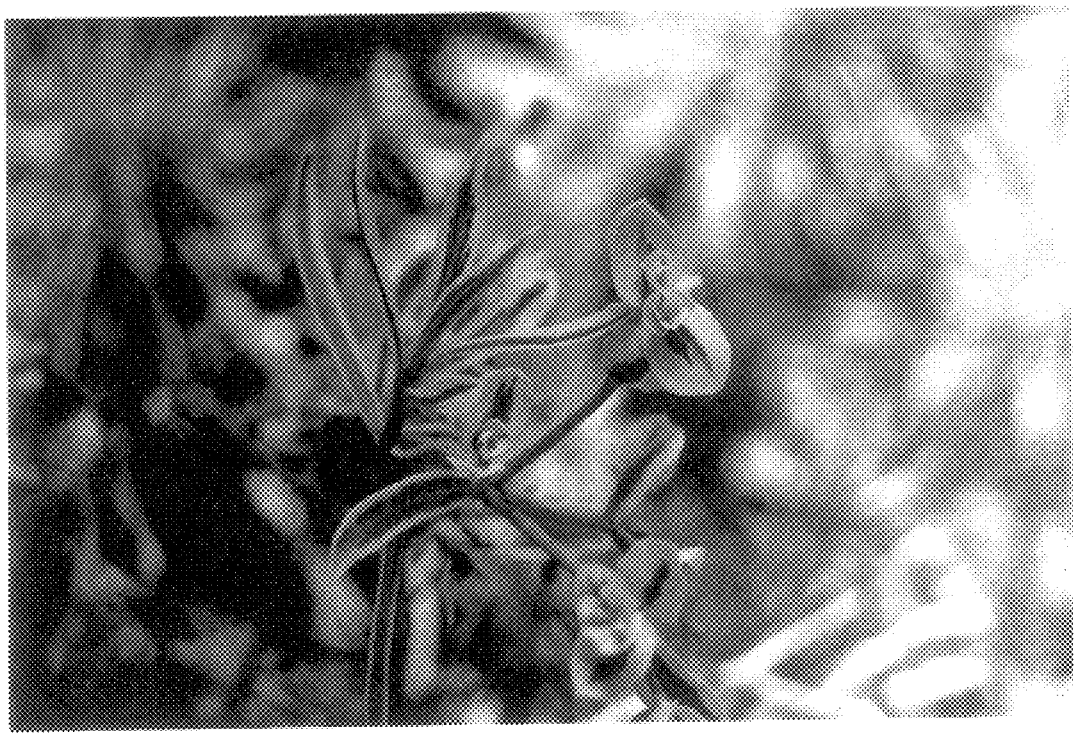

* * * * *